(12) United States Patent
Sutherland et al.

(10) Patent No.: US 10,500,236 B2
(45) Date of Patent: Dec. 10, 2019

(54) BIOACTIVE ANIMAL FEED

(71) Applicant: ECOLE POLYTECHNIQUE FEDERALE DE LAUSANNE (EPFL), Lausanne (CH)

(72) Inventors: Duncan-Bruce Sutherland, Lonay (CH); Mario Michael Zaiss, Rathsberg/Marloffstein (DE)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 15/559,177

(22) PCT Filed: Mar. 16, 2016

(86) PCT No.: PCT/IB2016/051473
§ 371 (c)(1),
(2) Date: Sep. 18, 2017

(87) PCT Pub. No.: WO2016/147121
PCT Pub. Date: Sep. 22, 2016

(65) Prior Publication Data
US 2018/0193390 A1   Jul. 12, 2018

(30) Foreign Application Priority Data
Mar. 16, 2015 (EP) .................... 15159277

(51) Int. Cl.
*A61K 35/74* (2015.01)
*A61K 35/66* (2015.01)
*A61K 35/741* (2015.01)
*A23K 50/50* (2016.01)
*A23K 50/80* (2016.01)
*A23K 10/18* (2016.01)
*A61K 9/00* (2006.01)

(52) U.S. Cl.
CPC .............. *A61K 35/74* (2013.01); *A23K 10/18* (2016.05); *A23K 50/50* (2016.05); *A23K 50/80* (2016.05); *A61K 9/0056* (2013.01); *A61K 35/66* (2013.01); *A61K 35/741* (2013.01)

(58) Field of Classification Search
None
See application file for complete search history.

(56) References Cited

U.S. PATENT DOCUMENTS

| 5,091,364 A | 2/1992 | Baumgarten et al. |
| 6,328,959 B1 | 12/2001 | Kayar et al. |
| 2012/0034198 A1* | 2/2012 | Garner ............... A61K 35/741 424/93.44 |
| 2014/0328803 A1 | 11/2014 | McKenzie et al. |

FOREIGN PATENT DOCUMENTS

| CA | 2893265 A1 | 6/2014 |
| EP | 2251017 A1 | 11/2010 |

OTHER PUBLICATIONS

Educational Materials Alginate Gel. http://www.psaalgae.org/alginate-gel/ retrieved Sep. 21, 2018.*
Khelaifia et al (PloS One 2013; 8(4):e61563).*
Drancourt. et al. Clinical Infectious Diseases 2017:65 (Jul. 1) pp. 1-5.*
Krajmalnik-Brown, Rosa, et al., "Effects of Gut Microbes on Nutrient Absorption and Energy Regulation", Nutr. Clin. Pract., Apr. 2012, vol. 27, No. 2, pp. 1-24.
Jun. 2, 2016 Search Report issued in International Patent Application No. PCT/IB2016/051473.
Jun. 2, 2016 Written Opinion issued in International Patent Application No. PCT/IB2016/051473.

* cited by examiner

*Primary Examiner* — Oluwatosin A Ogunbiyi
(74) *Attorney, Agent, or Firm* — Oliff PLC

(57) ABSTRACT

The invention relates to a food supplement comprising or consisting of Archaebacteria, and particularly methanogenic Archaebacteria, to be used as a probiotic adjunct for animal feed. The supplement can be provided to e.g. farmed animals in addition to standard feed or as a food composition. Such a supplement is particularly useful in aquaculture and proves able in increasing animal growth rates, reducing animal susceptibility to parasitic infections and/or ameliorating animal faecal waste impact on environment. Also encompassed by the present invention are methods of manufacturing a composition comprising the bioactive food supplement as well as uses thereof.

13 Claims, 5 Drawing Sheets

BIOACTIVE ANIMAL FEED

FIELD OF INVENTION

The invention pertains to the field of animal feed supplements, more specifically to a new feed composition comprising Archaebacteria and uses thereof.

STATE OF THE ART

Since the advent of commercial fish farming in the early 80ies, the aquaculture industry has grown to become an industry of major importance worldwide and is set to overtake capture fisheries as a source of food. The production in 2006 was reported to be 51.7 million tonnes with a value of US$ 78.8 billion, and has an annual growth rate of nearly 7 percent. According to FAO projections, it is estimated that in order to maintain the current level of per capita consumption, global aquaculture production will need to reach 80 million tonnes by 2050.

The continued growth of the aquaculture industry has presented the industry with a new range of challenges. Environmental, health and quality concerns related to the impact of the growing aquaculture industry have remained unresolved despite significant effort being invested. An environmentally sustainable aquaculture industry that minimizes risks to the marine environment and use of antibiotics is a prerequisite for long-term growth and development.

Animal farming, notably fish and poultry, is fraught with challenges related to infectious disease. These challenges include frequent loss on mass scale of animal harvests due to infectious transmission of pathogens as well as heavy dependence on toxic antibiotic-type drugs. Fish, poultry and other farmed animals are typically administered antibiotics-type drugs to increase stock yields even though excessive antibiotic use in farmed animals is not desirable or healthy for consumers. Outbreaks of infectious diseases occur frequently in the aquaculture industry and disease transmission is rapid due to the high density of animals in farms. Fish farmers administer antibiotics and other antimicrobial drugs as a means to contain disease transmission. This practice makes fish more resistant to the antibiotics and drugs (over-dependence) and consequently farmers are forced to increase dosages over time. Moreover, massive use of antimicrobials increases selective pressure on microbes and encourages natural emergence of bacterial resistance. Often, therefore, even large doses of antibiotics are unable to prevent large-scale mortality in fish farms. As a consequence of the above, it is evident that emphasis should be place on prevention, which is in fact more cost-effective than cure. Antimicrobials, disinfectants and pesticides largely treat symptoms of the problem, but not the cause. Moreover, waste products from animal farms also impact strongly on the environment—for example, fish farms contaminate water systems by generating excessive nitrate.

Developing a sustainable animal farming technology that increases product yield such as animal growth rate due to e.g. increased energy yield from diet, quality, and that can also reduce environmental impact is a major global challenge, and will likely result in more environmentally sustainable practice.

The gut microbiota refers to the microbe populations colonizing the intestine of humans and animals (Eckburg et al, Science 308: 1635-1638, 2005). It contains tens of trillions of microorganisms, including at least 1000 different species of known bacteria with more than 3 million genes (150 times more than human genes) and in humans the gut microbiota can weigh up to 2 kg. That the role of the gut microbiota in animals is important and that it impacts on many physiological functions that have a direct impact on health has been highlighted in recent scientific publications (Chervonsky, Immunological reviews 245: 7-12, 2012; Geuking et al, Gut microbes 5: 411-418, 2014; Hooper et al, Science 336: 1268-1273, 2012). These benefits include, among others, helping to digest certain nutrients, helping prevent infection by pathogenic microorganisms or playing an important role in the development and the maintenance of the immune system.

Taking into account the impact the gut microbiota has on growth and health performance, it has initiated a new approach of modulating the gut microbiota composition in fish in favour of better growth and improved resistance to infections in the aquaculture industry (Nayak, Fish & shellfish immunology 29: 2-14, 2010). The common use of broad-spectrum antibiotics in animal husbandry, while essential in many cases, can disrupt the indigenous gut microbiota making the animals more susceptible to antibiotic resistant pathogens.

In mammals, the gut microbiota is dominated by two divisions of bacteria, the Bacteroidetes and the Firmicutes, which together encompass 90‰of all phylogenetic types (phylotypes). Archaea are also represented in gut microbiota, most prominently by a methanogenic Euryarchaeote, *Methanobrevibacter smithii*, which comprises up to 10% of all anaerobes in the colons of healthy adults (Eckburg et al, 2005; Miller et al, Applied and environmental microbiology 51: 201-202, 1986), while *Methanosphaera stadtmanae* are less dominant and are minor members (Rieu-Lesme et al, Current microbiology 51: 317-321, 2005). Archaea are single celled microorganisms able to promote metabolic activity of healthy gut microbiota that aid in digestion (Dridi et al, PloS one 4: e70632009; Samuel et al, Proceedings of the National Academy of Sciences of the United States of America 104: 10643-10648, 2007).

To date the main bioactive components incorporated into fish pellet production include PUFAs (Polyunsaturated fatty acids), oils, phospholipids, proteins and peptides, fibres, carbohydrates, chitosans, vitamins and minerals, fucoxantin, polyphenols, phytosterols and taurine. These components have been demonstrated to improve resistance to hypertension, oxidative stress, inflammation, cardiovascular disease, cancer and other diseases. However, since the early 80ies, the use of probiotics has been proposed as a food source as well as a biological control agent. A probiotic is a live microbial feed supplement which, when administered in adequate amounts, confer a health benefit on the host. The concept was introduced in the first part of the last century, by claiming that the dependence of the intestinal microbes on the food makes it possible to adopt measures to modify the flora in animal bodies and to replace the harmful microbes by useful microbes. Commonly claimed benefits of probiotics include the decrease of potentially pathogenic gastro-intestinal microorganisms, the reduction of gastrointestinal discomfort, the strengthening of the immune system, the improvement of the skin's function, the improvement of bowel regularity, the strengthening of the resistance to cedar pollen allergens, the decrease in body pathogens, the reduction of flatulence and bloating, the protection of DNA, the protection of proteins and lipids from oxidative damage, and the maintaining of individual intestinal microbiota in subjects receiving antibiotic treatment.

A more detailed definition of probiotics relates to microorganisms that beneficially affect a host animal by modifying the host-associated or ambient microbial community, by insuring improved use of feed or by enhancing its nutrition, by enhancing the host response towards disease, or by improving quality of the ambient environment. This definition is especially appropriate when it comes to aquaculture. In fact, contrary to the terrestrial environment, where the gut represents a moist habitat in a water-limited world, in aquatic environments hosts and microorganisms share the ecosystem. Therefore, the environment for aquatic animals has much greater influence on microbiota than with terrestrials, and bacteria in aquatic medium heavily influence composition of host's gut microbiota. Aquatic animals are surrounded by an environment supporting their pathogens independently of the host animal, and opportunistic pathogens can therefore reach high densities around the fish, thus being commonly ingested with the feed or via drinking. Moreover, contrary to terrestrials which have inherent colonizing bacteria from the mother, aquatics largely spawned as axenic eggs. Ambient bacteria colonize eggs surface, and young larvae often have no developed gut (e.g., shrimp) and/or no microbial community in gut, gills or skin. As a consequence, since properties of bacteria in ambient water are very important, improvement of the ambient environment is crucial for the wellness of the bred animals.

Many prior art documents report the use of microbial adjuncts in animal feed. CN103783267 provides a method of producing fishmeal using probiotics, by including in particular strains of *Bacillus, Lactobacillus*, yeast, actinomycetes and photosynthetic bacteria in one or more of combinations.

Similarly, CN103875977 discloses a mixed feed for aquaculture, including basic and compound feed bacteria, the amount of the compound bacteria being 1~10‰ material weight. The aquatic feed would be useful for regulating intestinal colonies of aquatic biological balance, preventing of gastrointestinal diseases, helping digestion and absorption and enhancing immunity and disease resistance, thus avoiding use of antibiotics and drugs. The composite bacteria component of the animal feed may include mass ratio of 5 to 7:2~3:1~2 of *bacillus*, lactic acid bacteria and *Clostridium*.

WO 2012/138477 discloses a method for reducing mortality in fish due to disease caused by a bacterium comprising administering to said fish either or both of strain C6-6, which has been designated Accession No. B-50481, and C6-8, which has been designated Accession No. B-50482, in an amount effective to reduce mortality due to disease caused by the bacterium. A feed for fish comprising either or both of bacterial strain C6-6 and C6-8 is also disclosed. These two *Enterobacter* strains are useful, individually or in combination with each other or with one or more other bacterial strains, as a probiotic for the treatment and prophylaxis or prevention of infectious diseases, such as coldwater disease, in salmonids.

CN102132788 relates to the use of probiotics bacteria, in particular the *Myxococcus fulvus* strain, for restraining the growth of pathogenic microorganism in aquaculture, increasing the efficiency of feed utilization by the fish, and reducing the mortality rate.

WO2012105804 discloses probiotics for biological control against *Vibrio* sp., and in particular, to a newly isolated *bacillus* strain that degrades quorum-sensing signal molecules of the pathogenic bacteria *Vibrio* sp., and inhibits biofilm formation. Among the objects of the invention, a probiotic composition, a feed additive, an antimicrobial agent, or a water quality improving agent comprising the strain are also claimed.

WO 2003/038109 discloses a method for inhibiting the growth of methanogenic Archaea as well as a method for increasing the feed efficiency in a ruminant animal.

Notwithstanding the great amount of work in the field of probiotics and animal feed supplements to improve and ameliorate conditions of farmed animals, there is still a need in the art for alternative compositions, especially in aquaculture, for preventing parasitic-derived pathologies as well as for enhancing the dietary energy yield and for amelioration of faecal waste quality.

SUMMARY OF INVENTION

The invention is based at least in part on the discovery that organisms belonging to the Archaea kingdom, especially methanogenic Archaebacteria, can be used as a natural bioactive supplement for animal feeds, particularly for farmed animals. According to one aspect of the invention, these microorganisms can be e.g. harvested from the gastrointestinal tracts of cattle such as ruminants and included within animal feed compositions as a probiotic adjunct, with the aim of harnessing and intensifying naturally occurring biological pathways that improve dietary energy yield and minimize disease, thereby reducing dependence on broadspectrum antibiotic treatments as well as reducing the environmental impact caused by animal faecal contamination. By using an established animal models, the inventors tested and verified that enrichment of methanogenic Archaea into an animal feed has the potential to improve growth rate and immunity response to parasitic infection in farmed animals. When administered to mice, the feed supplement increases growth rate and the gut mucosal barrier function of the model animals, which are more resistant to infection with the prototype intestinal parasite *H. polygyrus*. In aquatic animals such as fish or crustaceans, in addition to the mentioned advantages, a faster growth rate, a higher digestion/absorption of feed and feed conversion ratio, as well as a reduced amount of pollutants in tank water can be clearly shown. Such a bioactive adjunct proved therefore able to (i) improve energy harness leading to better growth rates, (ii) increase resistance to infections by reducing the need for broad-spectrum antibiotic treatments and (iii) improve quality of discharges resulting in less impact on the environment.

Accordingly, it is an object of the present invention to provide for a bioactive food supplement for use in animal farming feed, characterized in that it comprises at least one population of at least one Archaebacteria species.

In a preferred embodiment, the at least one Archaebacteria species of the bioactive food supplement is a methanogenic Archaebacteria species. In a more preferred embodiment, the methanogenic Archaebacteria species is the *Methanosphaera stadtmanae* species or the *Methanobrevibacter smithii* species.

In one embodiment, the bioactive food supplement is further characterized in that, compared to standard farming conditions, it increases animal growth rates and/or reduces animal susceptibility to parasitic infections and/or ameliorates the animal faecal waste impact on environment.

In one embodiment, the bioactive food supplement is further characterized in that it is substantially enriched in Archaebacteria species.

Another object of the present invention is to provide for a composition comprising the bioactive food supplement as previously described. In one embodiment, the above-mentioned composition is characterized in that it is in a solid form. In one embodiment, the composition is characterized in that it comprises between about $10^5$ and about $10^8$ Archaebacteria cells per gram of composition.

A further object of the present invention relies in a method of manufacturing a composition comprising the bioactive food supplement as previously defined, characterised in that it comprises the steps of:
- Obtaining at least one population of at least one Archaebacteria species; and
- Mixing said at least one population of at least one Archaebacteria species with a carrier.

In one embodiment of the said method, the carrier comprises or consists of an aqueous solution, an oil, an Archaebacteria culture medium and/or rumen fluid.

In a particular embodiment of the invention, the method is characterised in that the carrier is a liquid carrier, and further comprises the steps of:
- Adding between 1% to 10% w/v of a thickening agent to the liquid composition comprising the liquid carrier and the at least one population of at least one Archaebacteria species;
- Mixing the liquid composition to obtain a thickened solution; and
- Drying the thickened solution to obtain a solid composition.

In another embodiment, the thickening agent is a sugar, starch and/or gelatin. In a particular embodiment, the at least one population of at least one Archaebacteria species is obtained by isolation from rumen extract.

An additional object of the present invention relies in a composition for use as an animal farming feed obtained through the above described method.

A further object of the present invention relates to a method for increasing growth rates of farmed animals, a method for reducing susceptibility to parasitic infections of farmed animals and a method for ameliorating the farmed-animals faecal waste impact on environment, each of these methods comprising the step of providing to the farmed animals a bioactive food supplement or a composition as described above.

An additional object of the present invention relates to a population of methanogenic Archaebacteria species for use in the manufacture of a bioactive food supplement for use in animal farming feed.

In a preferred embodiment of the invention, the farmed animals referred to in the above described bioactive food supplement, composition, methods and population are birds, mammals or aquatic animals.

As mentioned the food supplement according to the present invention may be advantageously used in animal farming. The invention is however not limited to this use. The food supplement may also be administrated to pets, captive animals or human beings.

DESCRIPTION OF EMBODIMENTS

Figure 1:
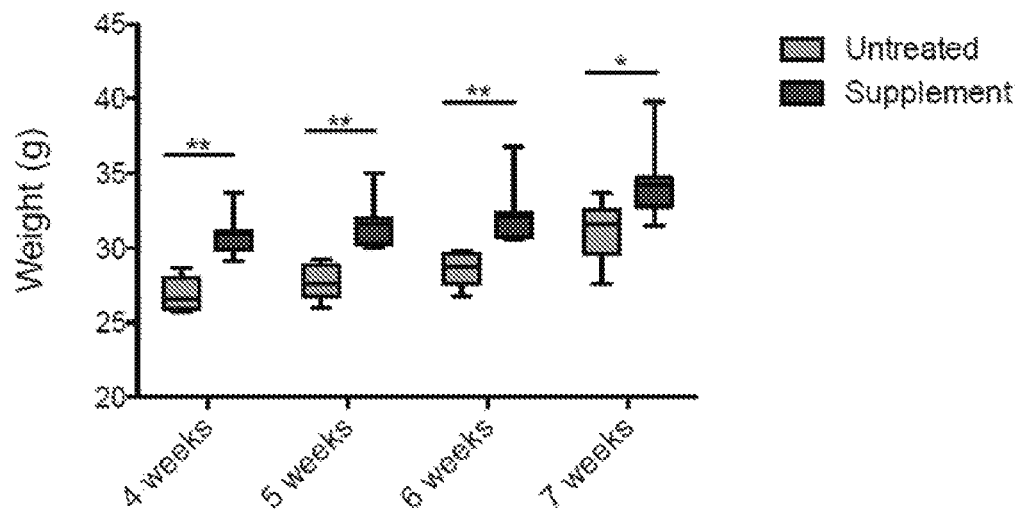
FIG. 1 shows that the bioactive food supplement promotes body weight gain in naïve wild-type mice. Specific-pathogen-free (SPF) housed female C57BL/6 mice (n=6) at 6-weeks age were fed grain-based chow containing the bioactive food supplement or untreated control for 7-weeks and body weight was measured. Body weight was not significantly different between the groups at the start of the experiment. Body weight was significantly elevated in mice after 4-weeks of receiving the bioactive food supplement compared to untreated mice. Body weight of supplemented mice remained elevated for the remainder of the experiment.

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a," "and," and "the" include plural referents unless the context clearly dictates otherwise. Thus, for example, reference to "a composition" includes a plurality of compositions and reference to "a probiotic" includes reference to one or more probiotics, and so forth.

Also, the use of "or" means "and/or" unless stated otherwise. Similarly, "comprise", "comprises", "comprising", "include", "includes", and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

In the frame of the present disclosure, a "bioactive food supplement", hereinafter also referred to sometimes as just "the supplement", is any type of food supplement comprising an active agent. The expression "active agent", as well as "bioactive compound", refers to any chemical or biological entity that is biologically active, i.e. having an effect upon a living organism, tissue, or cell. The expression is used herein to refer to any compound that alters, inhibits, activates, or otherwise affects biological or chemical events. In particular, an active agent or bioactive compound according to the present invention acts substantially as a probiotic, i.e. by beneficially affecting a host animal by modifying the host-associated or ambient microbial community, by insuring improved use of feed or by enhancing its nutrition, by enhancing the host response towards disease, or by improving quality of the ambient environment. More particularly, in the frame of the invention, the bioactive compound characterising the bioactive food supplement comprises at least one population of at least one Archaebacteria species.

The term "population" as used herein relates to a group of individual organisms of the same species defined by time and space. However, the term can be also intended as a community, i.e. a group of organisms inhabiting a particular ecological niche, which could include any number of species. In this context, the term "population" is also referred to as a "mixed population". As will be apparent to a person skilled in the relevant art, a population of Archaebacteria species for inclusion into a bioactive food supplement can be obtained, if a commercially-available alternative is not envisaged, through any common isolation method, including the serial dilution method, streak plate method, pour plate/spread plate method, enrichment culture method, methods exploiting selective media, methods exploiting differential media and so forth.

In a preferred embodiment according to the invention, the active agent of the bioactive food supplement is a methanogenic Archaebacteria species, that is, Archaebacteria species that produce methane as a metabolic by-product in anoxic conditions. Methanogens are a diverse group of strict anaerobes which are widely distributed in nature and can be found in a variety of permanently anoxic habitats like flooded soils, sediments, sewage-sludge digestors or the digestive tract of certain animals. All known methanogens are affiliated to the Archaea and extremely sensitive to oxygen. The hallmark feature of methanogens is the reduction of C-1 compounds (e.g., $CO_2$, methanol, formate, or N-methyl groups) to methane ($CH_4$). Methanogens play a vital ecological role in anaerobic environments of removing excess hydrogen and fermentation products that have been produced by other forms of anaerobic respiration. Methanogenic Archaea also play a pivotal role in ecosystems with organisms that derive energy from oxidation of methane, many of which are bacteria, as they are often a major source of methane in such environments and can play a role as primary producers. Methanogens also exert a critical role in the carbon cycle, breaking down organic carbon into methane, which is also a major greenhouse gas. Methanogenesis also occurs in the guts of humans and other animals, especially ruminants. In the rumen, anaerobic organisms, including methanogens, digest cellulose into forms usable by the animal. Without these microorganisms, animals such as cattle would not be able to consume grass. The useful products of methanogenesis are absorbed by the gut, while methane is released by the animal.

A list of methanogenic Archaea species comprises *Methanobacterium bryantii, Methanobacterium formicum, Methanobrevibacter arboriphilicus, Methanobrevibacter gottschalkii, Methanobrevibacter ruminantium, Methanobrevibacter smithii, Methanococcus chunghsingensis, Methanococcus burtonii, Methanococcus aeolicus, Methanococcus deltae, Methanococcus jannaschii, Methanococcus maripaludis, Methanococcus vannielii, Methanocorpusculum labreanum, Methanoculleus bourgensis, Methanoculleus marisnigri, Methanoflorens stordalenmirensis, Methanofollis liminatans, Methanogenium cariaci, Methanogenium frigidum, Methanogenium organophilum, Methanogenium wolfei, Methanomicrobium mobile, Methanopyrus kandleri, Methanoregula boonei, Methanosaeta concilii, Methanosaeta thermophila, Methanosarcina acetivorans, Methanosarcina barkeri, Methanosarcina mazei, Methanosphaera stadtmanae, Methanospirillium hungatei, Methanothermobacter defluvii, Methanothermobacter thermautotrophicus, Methanothermobacter thermoflexus, Methanothermobacter wolfei* and *Methanothrix sochngenii*. In one embodiment, the Archaebacteria species used as active agent for the bioactive food supplement of the invention is the *Methanosphaera stadtmanae* species and/or the *Methanobrevibacter smithii* species.

The bioactive food supplement of the invention is characterized by the fact of comprising at least one population of at least one Archaebacteria species. However, several other agents can be present in the supplement, particularly other kind of probiotics. This is especially true when, as will be detailed later on, said Archaebacteria population has been obtained from cattles' rumen extracts, where a blend of several microorganisms (generally named microbiota) can be present. Without being necessarily bound to this theory, some observations made by the present inventors suggest that Archaebacteria populations maintain a positive symbiotic relationship and promote suitable environmental growth/proliferation conditions of a so called "Archaea associated microbiota" (i.e. an ensemble of microorganisms that usually establish a symbiotic tie in a selected environment with Archaeabacteria, including for example anaerobic/fermenting probiotics), particularly in terms of preservation of a complex population comprising more types of anaerobic microorganisms. An equilibrium between more than one probiotic in a food supplement enriched in Archaebacteria according to the invention is possibly one of the key features of the noticed positive effects of the supplement of the invention on farmed animals.

Accordingly, in some preferred embodiments of the invention, the bioactive food supplement is characterized by the fact that it is substantially enriched in Archaebacteria species. As used herein, "substantially enriched" means that the population of Archaea cells within the supplement of the invention is at least 1% of the total microbial probiotic cells, preferably between about 2 and about 10% of the total microbial probiotic cells. This enrichment has the beneficial effect described above when more than one microorganism population, preferably of probiotic microorganisms, is present in the composition. In some embodiments, higher percentages such as 15, 20, 30, 40, 50, 60, 70, 80, 90 up to 100% of the microbial cells present in the supplement are Archaea cells, i.e. the bioactive food supplement does not contain any other microorganism, including probiotic ones.

As said, the bioactive food supplement of the invention acts as a probiotic. Particularly, one aim of the bioactive food supplement of the invention is boosting and/or enhancing certain aspects of the physiology of farmed animals, as well as the consequent impact said ameliorated physiology-related conditions have on the surrounding environment. As explained in the background section, this is especially true in the aquaculture, where the farmed animals (in this case, aquatic animals such as for example fishes, eels or crustaceans) have an extremely tight relationship with the environment they are farmed in. However, farmed animals according to the invention can also be birds such as chickens, fowls, ostriches and the like, or mammals as for example domesticated animals such as cattle, sheep, pigs, horses, rodents and the like, and also possibly primates and humans. Accordingly, the bioactive food supplement is characterised by the fact that it acts on physiological animal parameters, by positively affecting them so that farming conditions are advantageously improved compared to standard farming conditions. In particular, the bioactive food supplement of the invention results useful in increasing animal growth rates and/or in reducing animal susceptibility to parasitic infections and/or in ameliorating the animal faecal waste impact on environment. These useful properties of the invented supplement have been shown, as will be detailed below in the Examples section, in both mammalian and aquatic animal models fed with the supplement for a suitable time period, thus supporting the above-mentioned advantageous features. Therefore, in addition, it is one aim of the invention to provide for methods for increasing animal growth rates, reducing animal susceptibility to parasitic infections or ameliorating the animal faecal waste impact on environment, said methods comprising the step of administering the bioactive food supplement, or a composition comprising thereof, to a farmed animal.

For what said above, therefore, according to one aspect of the invention it is also provided a composition characterised in that it comprises the bioactive food supplement of the invention. In the frame of the present disclosure, the term "composition" is used interchangeably with the term "formulation". A "composition", as used herein, refers to a mixture of ingredients or compounds prepared in a certain way and used for a specific purpose. The concept is also clearly linked to the process in which different compounds, including the active agent, are combined to produce a final product. Usually, since the ingredients impart peculiar properties to the final product (i.e., the final composition) when it is put into use, said ingredients are mixed according to a specific formula in order to obtain characteristic features for the final composition, such as e.g. the achievement of effects that cannot be obtained from its components when these are used singly, a higher degree of effectiveness to facilitate any potential synergistic action of their components, to improve handling properties and/or safety for end user and the like.

The compositions of this invention may be in a variety of forms, the preferred form usually depending on the intended mode of administration and/or intended application. Compositions normally comprise at least one acceptable carrier for the active agent (and which can also serve, in case, as a diluent means), excipients and so forth. As used herein, an "acceptable carrier" is any agent acting as a delivery means as well as, if needed, a dispersing means for the active agent. The term includes any and all solvents, liquid diluting agents, absorption delaying agents and the like, that are physiologically compatible with the end user, in this case a farmed animal, but also solid carriers as pre-constituted food pellet. Examples of suitable carriers are well known in the art and include aqueous solutions (e.g. sodium chloride solutions, phosphate buffered sodium chloride solutions and the like), water, oils such as fish oils, emulsions such as oil/water emulsions, various types of wetting agents and so forth.

A composition according to the present disclosure can be provided in liquid form. A liquid composition is a composition in which the carrier is a liquid carrier and which maintain a liquid form notwithstanding the presence of any another added excipient. A liquid formulation includes e.g. aqueous solutions, non-polar solutions or emulsions. An "aqueous solution" is a solution in which the solvent is substantially made of water. In the frame of the present disclosure, the term "aqueous" means pertaining to, related to, similar to, or dissolved in water. The expression also includes highly concentrated and/or viscous solutions such as for instance syrups (i.e., saturated water/sugars solutions) and the like, in which the water content is e.g. less than 5% weight of the total solution weight. A "non-polar solution" is a solution in which the solvent is a non-polar compound. Non-polar solvents are intended to be compounds having low dielectric constants and that are not miscible with water. Non-polar solutions can comprise for example oils. An "oil" is any non-polar chemical substance that is a viscous liquid at ambient temperatures and is both hydrophobic and lipophilic. Particularly suitable oils according to the present invention are fish oils. An "emulsion" is a mixture of two or more fluids that are normally immiscible (unblendable). Emulsions are part of a more general class of systems of matter called colloids. Although the terms colloid and emulsion are sometimes used interchangeably, in the frame of the present disclosure the term emulsion is used when both the dispersed and the continuous phase are fluids, such as e.g. liquids. In an emulsion, one fluid (the "dispersed phase") is dispersed in the other (the "continuous phase").

In one particular embodiment according to the present invention, the composition comprising the bioactive food supplement of the invention comes in a solid form, i.e. a formulation in which the carrier is a solid carrier or wherein the content of a liquid carrier (or a liquid composition) and/or the presence of further excipients into a liquid carrier (or a liquid composition) is such as to create a non-fluid composition. This includes among others also semi-solid compositions, lyophilized compositions, putty-like formulations, gel-like materials, composite hydrogels and the like. As used herein, the term "gel" refers to a non-fluid colloidal network or polymer network that is expanded throughout its whole volume by a fluid. A gel is a solid three-dimensional network that spans the volume of a liquid medium and ensnares it through surface tension effects. The internal network structure may result from physical bonds (physical gels) or chemical bonds (chemical gels). As used herein, the term "hydrogel" refers to a gel in which the swelling agent is an aqueous solution. A hydrogel is a macromolecular polymer gel constructed of a network of crosslinked polymer chains. It is synthesized from hydrophilic monomers, sometimes found as a colloidal gel in which water is the dispersion medium. Hydrogels are highly absorbent (they can contain over 90% of an aqueous solution) natural or synthetic polymeric networks. As a result of their characteristics, hydrogels develop typical firm yet elastic mechanical properties.

A solid composition can also be created, as said, via the addition of particular excipients to a liquid carrier or a liquid composition. This approach is especially advantageous when, as should be the case for the present invention, an active agent is already comprised in a liquid solution. In one embodiment of the invention, in fact, Archaebacteria (as a matter of fact, the active agent of the invention) are cultured in a liquid culture medium (also referred to as a "broth"). If a solid composition is intended to be used for animal feeding, such a liquid culture medium can be solidified or thickened by the addition of a thickening agent. A "thickening agent" or "thickener" is a substance which can increase the viscosity of a liquid without substantially changing its other properties. Thickeners may also improve the suspension of other ingredients or emulsions which increases the stability of the product. Food thickeners are frequently based on either polysaccharides (starches, vegetable gums, and pectin), or proteins. This category includes starches as arrowroot, cornstarch, katakuri starch, potato starch, sago, tapioca and their starch derivatives. Vegetable gums used as food thickeners include alginin and salts thereof (e.g. alginic acid (E400), sodium alginate (E401), potassium alginate (E402), ammonium alginate (E403), calcium alginate (E404)), guar gum, locust bean gum, and xanthan gum. Proteins used as food thickeners include collagen, egg whites, furcellaran, and gelatin. Sugars include agarose, trehalose, sucrose, glucose, mannitol and carrageenan. Some thickening agents are gelling agents (gellants), forming a gel, dissolving in the liquid phase as a colloid mixture that forms a weakly cohesive internal structure. Typical gelling agents include e.g. natural gums, starches, pectins, agar-agar and gelatin. Different thickeners may be more or less suitable in a given application, due to differences in taste, clarity, and their responses to chemical and physical conditions. In a preferred embodiment of the invention, a thickening agent included in feed compositions is selected from a sugar, gelatin and/or starch.

A composition usually includes, depending on particular needs, other components such as for instance organic acids or their salts; antioxidants such as ascorbic acid; low molecular weight (less than about ten residues) (poly)peptides, e.g., polyarginine or tripeptides; proteins such as those derived from a vegetal source such as soy; amino acids, such as glycine, glutamic acid, aspartic acid, lysine, methionine, tryptophan or arginine; monosaccharides, disaccharides, and other carbohydrates including cellulose or its derivatives, glucose, mannose, or dextrins; sugar alcohols such as mannitol or sorbitol; vitamins; oils such as soybean oil; fatty acids; phospholipids and/or ions such as sodium.

In some embodiments of the invention, a solid composition can also be conceived so to be solubilized later on in water, such as drinking water, in order to have a simple, on demand delivery mean for farmed animals such as chickens and pigs, while keeping all the advantages of solid formulations (ease of storage, precise dosage, vacuum packaging and the like).

Independently of the formulation form, one important aspect of the compositions of the invention is its Archaea cells content, which is conceived in order to exert a physiological effect typical of probiotics. In preferred embodiments of the invention, the composition is characterized in that it comprises between about $10^5$ and about $10^8$ Archaebacteria cells per gram of composition. On this basis, the dosage can be optimised according to several parameters such as type of animal, its diet, its weight and so forth. Anyway, the above concentration range is not limiting, and lower or higher ranges can be envisaged in the frame of the present disclosure. In one scenario, the bioactive food supplement of the present invention can be mixed with e.g. a pre-formed or commercially available feed for farmed animals: keeping between about $10^5$ and about $10 8$ Archaebacteria cells per gram of final animal feed upon mix is considered a preferred embodiment.

A further aspect of the invention relies in methods for manufacturing a composition according to the present invention, as well as compositions obtained through said methods. Generally speaking, according to the invention, a method for manufacturing a composition suitable as an animal feed comprises the steps of obtaining at least one population of at least one Archaebacteria species and mixing it with a suitable carrier. Depending on the needs, the carrier can be a liquid carrier or a solid carrier, so that a liquid formulation or a solid formulation can be obtained.

As would be evident for a skilled person, a population of at least one Archaebacteria species can be obtained with any known method, such as purchase on the trade of isolated Archaebacteria strains (including lyophilized forms thereof), culture of Archaebacteria in suitable culture broths (such as for instance, the *Methanosphaera* Medium I or the *Methanobacterium* Medium from the Leibniz Institute DSMZ—German Collection of Microorganisms and Cell Cultures GmbH) with or without a pelleting step, and the like. Additionally or alternatively, Archaebacteria can be obtained from other sources such as for instance isolation from the rumen extract of e.g. cattles. The rumen extract represents a perfect culture medium for Archaebacteria since it contains nutrients that nourish the microorganisms (especially methanogenic Archaea) under perfect culture conditions—anaerobic conditions in the cow rumen. Through routine lab procedures, large amounts of rumen extract can be extracted from one cow per day; this can be possibly sterilized (through e.g. exposure to oxygen and/or extreme temperatures) and a rumen fluid obtained therefrom can be used as the basis to cultivate Archaebacteria under anaerobic, controlled lab conditions. Moreover, the high functional potential of the cow's methanogenic microbiota can be preserved even when obtained readily post-mortem from cattles, and then harnessed to promote better digestion of plant-based diets and immune system activation for farmed animals such as chickens, pigs and fish. For instance, the anaerobic rumen microbiota of cows post-mortem can be extracted from the rumen by mechanical pressing so to obtain a rumen fluid enriched with methanogenic Archaea; this can be mesh filtered and possibly eventually preserved by routine freeze-dry or spray-dry method using a suitable cryoprotectant (sugar, starch, gelatin etc).

Once obtained a population of at least one Archaebacteria species, this is mixed with a carrier, either a liquid or a solid one. In certain aspects, particularly when a liquid composition is envisaged, the carrier can even be the same culture broth and/or a rumen fluid obtained from the rumen extract after an extraction process (e.g., pressing of the rumen extract) where the microorganisms have been cultured.

In a particular embodiment of the invention, in order to obtain a solid composition starting from a liquid one, additional steps can be performed. A specific method according to the invention foresees the addition of between 1% to 10% w/v of a thickening agent to the liquid composition comprising the liquid carrier and the at least one population of at least one Archaebacteria species, mixing with any suitable means (e.g. a stirrer) the so-obtained liquid composition/thickener to obtain a thickened solution, with or without heating of the liquid composition, and drying the thickened solution to obtain a solid composition. Said solid composition can be hereinafter shaped in the most convenient way as to obtain sticks, blocks, pellets, granules, (micro)sphere and so on.

For the sake of better clarifying the following paragraphs, a "Peyer's patch" is a roughly egg-shaped lymphatic tissue nodule that is similar to lymph nodes in structure, except that it is not surrounded by a connective tissue capsule. Peyer's patches belong to a class of non-encapsulated lymphatic tissue known as lymphatic nodules, which include the tonsils and lymphatic tissue of the appendix. Special epithelial cells known as microfold cells (M cells) line the side of the Peyer's patch facing the intestinal lumen, while the outer side contains many lymphoid cells and lymphatic vessels. The function of Peyer's patches is to analyze and respond to pathogenic microbes in the ileum. Antigens from microbes in the gut are absorbed via endocytosis by M cells lining the surface of each Peyer's patch. These antigens are passed on to the lymphoid tissue, where they are absorbed by macrophages and presented to T lymphocytes and B lymphocytes. When presented with dangerous pathogenic antigens, lymphocytes trigger the immune response by producing pathogen-specific antibodies, turning into pathogen-killing cytotoxic T lymphocytes and migrating through lymphatic vessels to lymph nodes to alert the other cells of the immune system. The body then prepares a full body-wide immune response to the pathogen before it is able to spread beyond the intestines. Peyer's patches, like other components of the lymphatic system, can become inflamed or ulcerated when the tissue surrounding them becomes inflamed, rendering them permeable to toxins and foreign bacteria.

EXAMPLES

Example 1

To describe and illustrate more clearly the present invention, the following examples are provided in detail, which however are not intended to be limiting of the invention. In the exemplary embodiment herein described, harvesting and preparation of bioactive components of the invention from the rumen of cattle is performed to improve feed pellets for mice. This is achieved by isolation and subsequent incorporation of naturally occurring Archaea from bovine rumen into mice feed.

Methods

Mice: Female C57BL/6 mice commenced treatments at 8 weeks age. Body weight was measured periodically and mouse wellbeing was closely monitored.

Bioactive food supplement production: The *Methanosphaera stadtmanae* strain DSZM 3091 and *Methanobrevibacter smithii* strain DSMZ 861 were purchased from the German Collection of Microorganisms and Cell Cultures (DSMZ, Braunschweig, Germany) both belonging to the Kingdom: Archaea; Phylum: Euryarchaeota; Class: Methanobacteria; Order: Methanobacteriales; Family: Methanobacteriaceae. They had been grown in liquid medium 322 and 119 (DSMZ, Braunschweig, Germany) respectively following the special instructions of cultivation of methanogens and special instructions of cultivation of anaerobes (DSMZ, Braunschweig, Germany) under anaerobic conditions at 37° C. in hungate tubes under a 2-bar $H_2/CO_2$ (80%-20%) atmosphere with agitation.

Bioactive food supplement administered as supplement feed: Each mouse cage was fed ad libitum with special prepared feed pellets. 500 ml from each *Methanosphaera stadtmanae* and *Methanobrevibacter smithii* liquid cultures were harvested from cultivation bottles after 5 days of incubation, and combined with 5 g of agarose/gelatin and mixed to produce a solid product. The agarose/gelatin-bioactive food supplement mix was mechanically crushed into solid pieces of about 2-4 mm diameter. 19 kg of standard mouse feed pellets were dissolved in 6 L distilled $H_2O$ and the agarose/gelatin bioactive food supplement mix was added later on. The complete mixture was agitated for 5 minutes to obtain a homogeneous mass. This mass was reduced in pieces of 0.5×1 cm, spread on aluminium foil and dried over night at 21° C.

*H. polygyrus* model: C57BL/6 were bred and maintained under specific pathogen-free (SPF) conditions. All mice were fed with standard breeding diets prior to the start of the experiment. To standardize the intestinal bacteria within different groups of SPF mice analyzed within one experiment, all mice were co-housed for 3 weeks prior to parasite infection. Mice were then infected orally with 200 L3 *Heligmosomoides polygyrus bakeri* (Hpb) and diets simultaneously changed to either the standard control diet or to experimental diet including the bioactive food supplement as previously described. After Hpb infection, co-housing or bedding mixes were stopped for the rest of the experiments. Egg production was quantified throughout the experiment by collection of moist faecal flotation using saturated NaCl, and eye-counted using a McMaster Worm Egg Counting Chamber (Weber Scientific International, Ltd, Hamilton, N.J., USA). At the end of the experiment, animals were sacrificed and adult worm burdens as well as intestinal Peyer's patch sizes were determined by manual counting of the small intestinal contents and outer surface, respectively, by using a dissecting microscope.

Results

The Bioactive Food Supplement Promotes Weight Gain in Naïve Wild-type Mice

The effect of the bioactive food supplement on mouse body weight was tested (FIG. 1). Conventional feed was mixed with a 1% agar-based vehicle containing the supplement or with the agar-based vehicle alone as control. Mice were monitored for possible aversion to the agar-based vehicle and the bioactive food supplement. Mice showed no aversion to eating feed containing agar-based vehicle or supplement. Mouse weights were not significantly different at the starting point when the bioactive supplement was introduced. After 4-weeks on the respective feeds, mice receiving the supplement showed statistically significant weight gain compared to mice receiving the control vehicle.

The Bioactive Food Supplement Promotes Mucosal Immunity

Figure 2:
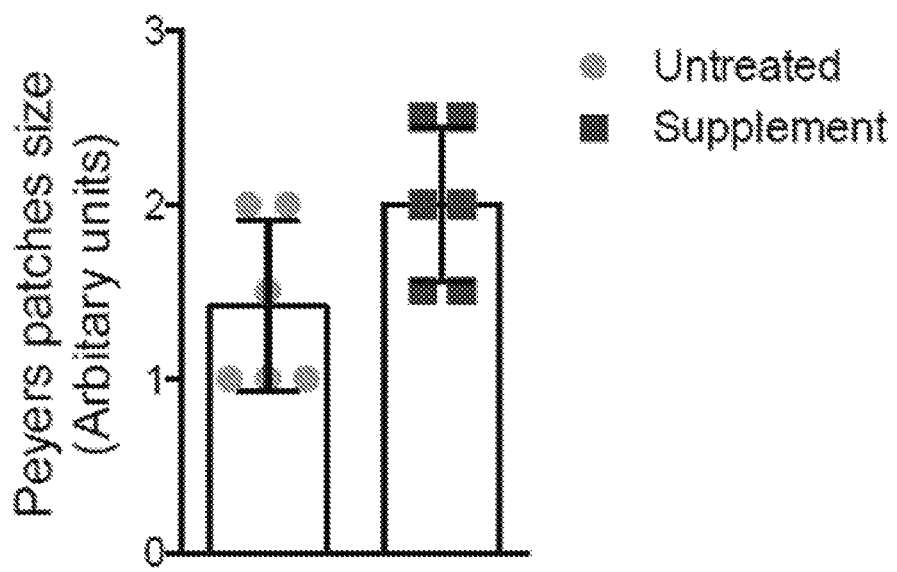
FIG. 2 shows that the bioactive food supplement promotes Peyer's patch size in naïve wild-type mice. SPF housed female C57BL/6 mice (n=6) at 6-weeks age were fed grain-based chow containing the bioactive food supplement or untreated control for 7-weeks and then mice were dissected and intestinal Peyer's patches were scored based on size. Mice that received the diet containing the bioactive food supplement had clearly larger Peyer's patches.

The effect of bioactive food supplement on mouse small intestine mucosal immunity was tested (FIG. 2). The intestine is a common route of pathogen entry in vertebrates, thus the mucosa forms an important barrier preventing pathogen invasion. Peyer's patches—lymphoid aggregates in the small intestine—are the preliminary site for generating mucosal antibody secreting cells in the intestine needed for mucosal barrier function as well as nurturing of the endemic microbiota. Since the size of Peyer's patches in mouse intestines is directly linked to mucosal antibody production and quality, inventors determined the Peyer's patch sizes in mice that had received either bioactive food supplement or the control vehicle for duration of 7 weeks. Peyer's patch sizes were ranked as either small, regular or enlarged and an average size score for each intestine was calculated. Each mouse small intestine normally has 7 Peyer's patches, and this was unchanged in the respective groups. The average size of Peyer's patches was higher in mice that received bioactive food supplement compared to mice that received control vehicle.

The Bioactive Food Supplement Increases Resistance Against Parasitic Infection

Figure 3:
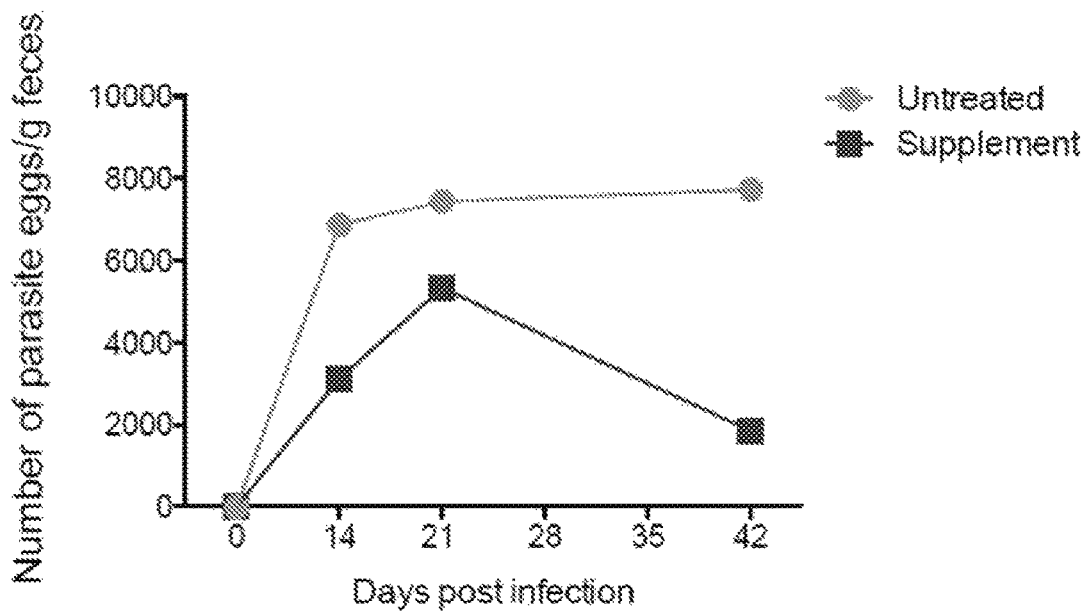
FIG. 3 shows that the bioactive food supplement increases resistance against the intestinal parasite *H. polygyrus*. SPF housed female C57BL/6 mice (n=6.4) at 6-weeks age were fed grain-based chow containing the bioactive food supplement or untreated control. Mice were then infected by gavage with 200 infectious units of *H. polygyrus* and the infectivity was determined between 2-6 weeks post infection by measuring faecal parasite egg counts. Mice treated with the bioactive food supplement in their diet had significantly reduced number of parasite eggs per gram faeces compared to the untreated group.
Figure 4:
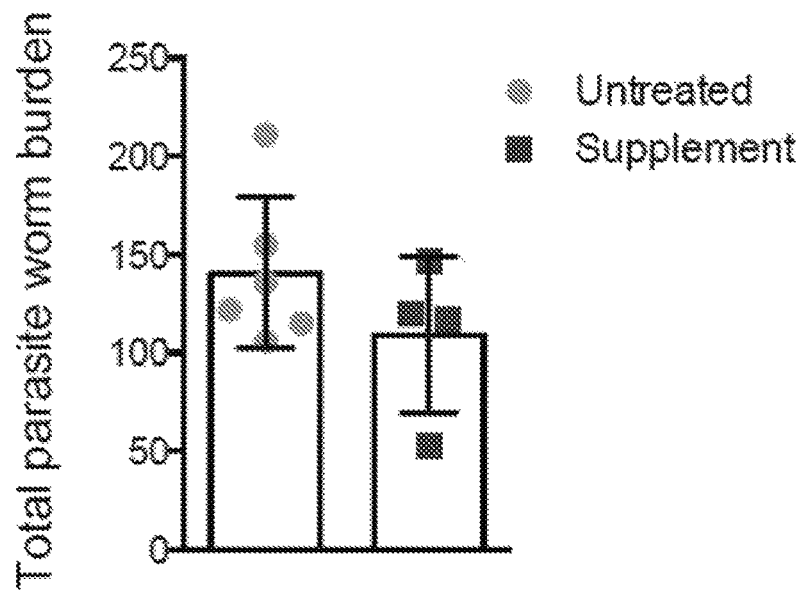
FIG. 4 shows that the bioactive food supplement reduces intestinal parasite burden in mice. SPF housed female C57BL/6 mice (n=4-6) at 6-weeks age were fed grain-based chow containing the bioactive food supplement or untreated control. Mice were then infected by gavage with 200 infectious units of *H. polygyrus* and the adult parasite burden was determined at 6-weeks post infection by dissecting and performing visual counts of parasites in the intestinal lumen. Parasite burden was clearly reduced in mice treated with the bioactive food supplement compared to the untreated group.

The effect of bioactive food supplement on resistance against a natural intestinal parasite was tested (FIGS. 3 and 4). Intestinal parasites (helminths) are a common burden in agriculture; therefore inventors used a prototype helminth infection, Hpb, to determine changes in infection susceptibility of mice that received bioactive food supplement in their diet. Hpb was administered orally according to a standardized model and worm fitness was determined by performing faecal worm egg counts between 2-4 weeks post infection. Mice receiving bioactive food supplement had significantly lower worm egg counts compared to mice that received the control vehicle only indicating increased parasite resistance in treated mice. At 4-weeks post infection, mice were sacrificed and dissected to determine the intestinal worm burden, another key parameter for determining host susceptibility to infection. The number of worms detected in bioactive food supplement-treated mice was significantly lower compared to mice that received control vehicle only, thus reinforcing the finding that bioactive food supplement increased resistance to the prototype intestinal parasite infection.

This study tested the potential to use the bioactive food supplement of the invention as a bioactive feed ingredient that can promote growth rate and innate disease resistance in farmed animals. The data clearly show that the supplement promotes both growth and resistance to infection in a well-established mouse model thus providing the first key proof of concept. Because the supplement harnesses naturally occurring biological interactions in the animal gut, it represents a physiologically as well as an ecologically safer alternative to current drug-based approaches for disease management in the agricultural industry.

The increased weight gain observed in mice receiving the bioactive food supplement is consistent with reports that methanogenic Archaea engage in biochemical symbiosis with bacteria to digest complex dietary carbohydrates, thereby increasing energy yield. The data do also provide evidence that the bioactive food supplement exerts its beneficial effects primarily in the gut lumen and/or mucus. First, the increased weight gain most likely results from increased dietary energy yield in the gut. Second, enhanced development of gut associated lymphoid tissues (Peyer's patches) result from localized changes in the intestinal microenvironment. Third, increased resistance was observed against an infection localized in the gut. By targeting the animal gut, the supplement is contained/localized, in contrast to antibiotic drugs that permeate the majority of host tissues.

The mucosal barrier plays an important role in preventing pathogen invasion but also has an important role in nurturing the endemic microbiota that have profound impacts on the host immune system that extends beyond the gut. Therefore, by promoting intestinal homeostasis, it could be anticipated that the bioactive food supplement is able to improve the overall immune system fitness, thus increasing immune resistance in a variety of tissues (epithelial surfaces, respiratory systems, fish gills etc).

Example 2

The effect of the bioactive supplement of the invention on the growth of pathogenic vibrios in vitro and on the virulence of these pathogenic vibrios in vivo has been assessed. In particular, the inventors used a culture dependent method to assess the antagonistic activity of the bioactive supplement against three selected pathogens in vitro and the gnotobiotic brine shrimp *Artemia* system to assess the protective effect of Archaeabacteria against the selected pathogen *V. harveyi* BB120 in vivo.

Bacterial Strains and Preparation

The pathogenic strains *Vibrio campbellii* LMG21363, *V. harveyi* BB120 and *V. parahaemolyticus* PV1 were used in the tests. All strains were preserved at −80° C. in Marine Broth 2216 (Difco Laboratories, Detroit, Mich. USA) with 20% sterile glycerol. The pathogenic vibrios were initially grown at 28° C. for 24 h on Marine Agar (Difco Laboratories, Detroit, Mich. USA) and then to log phase in Marine Broth by incubation at 28° C. with continuous shaking. A lyophilized composition of the invention was prepared with a concentration in Archaeabacteria of $10^{11}$ CFU $g^{-1}$.

Axenic Hatching of Brine Shrimp Larvae

Axenic larvae were obtained following decapsulation and hatching. Briefly, 2.5 g of *Artemia franciscana* cysts originating from the Great Salt Lake, Utah, USA (EG Type, batch 21452, INVE Aquaculture, Dendermonde, Belgium) were hydrated in 89 ml of distilled water for 1 h. Sterile cysts and larvae were obtained via decapsulation using 3.3 ml NaOH (32%) and 50 ml NaOCl (50%). During the reaction, 0.22 μm filtered aeration was provided. All manipulations were carried out under a laminar flow hood and all tools were autoclaved at 121° C. for 20 min. The decapsulation was stopped after about 2 min by adding 50 ml $Na_2S_2O_3$ at 10 g/L. The aeration was then terminated and the decapsulated cysts were washed with filtered (0.2 μm) and autoclaved artificial seawater (FAASW) containing 35 g/L of instant ocean synthetic sea salt (Aquarium Systems, Sarrebourg, France). The cysts were then suspended in a 1 L glass bottle containing FAASW and provided of 0.22 μm air filtration on the aeration inlet and outlet. The bottle was placed at 28° C. under constant illumination of approximately 2000 lux. The emerged larvae reaching stage II (at which time they start ingesting bacteria) were collected.

In Vitro Plate Assays

An aliquot (50 μL) of each of the pathogenic vibrios was plated on general growth agar (Marine Agar; MA) and minimal agar added with shrimp feed. The latter agar consisted of Nine Salts agar (NSA) supplemented with 500 mg/L shrimp feed (Crevetec PL500, Crevetec, Belgium) before sterilisation. After plating, the plates were left open under sterile conditions until dryness. Next, the composition of the invention was suspended in the respective growth medium (i.e. marine broth or Nine Salts Solution) at 100 mg/L (=107 CFU/mL) and a 50 μL aliquot was transferred onto a sterile inoculation disc that was placed at the centre of the agar plate. Each plate was sealed with parafilm and placed in an incubator at 28° C. The growth of the pathogenic vibrios was monitored over 48 hours and the appearance of clearing zones around the spotted disc was determined.

Figure 5:
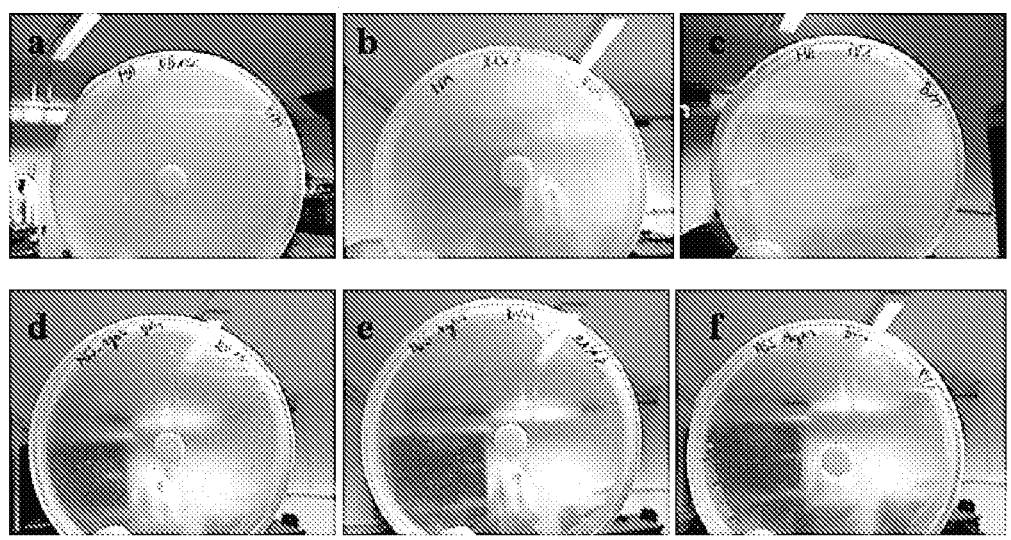
FIG. 5 shows an in vitro assay to determine the growth inhibitory effect of Archaea on three different pathogenic vibrios. Panel a: *V. harveyi* BB120 on Marine Agar; panel b: *V. campbellii* LMG21363 on Marine Agar; panel c: *V. parahaemolyticus* PV1 on Marine Agar; panel d: *V. harveyi* BB120 on Nine Salts Agar; panel e: *V. campbellii* LMG21363 on Nine Salts Agar; panel f: *V. parahaemolyticus* PV1 on Nine Salts Agar.

On each of the inoculated agar plates, the growth of the pathogen could clearly be observed. However, none of the plates showed a clearing zone indicating growth inhibition around the disc spotted with the Archaea as can be seen in FIG. 5.

In Vivo Challenge Assay

In this experiment, the protection of *Artemia* nauplii against a challenge with the selected pathogen *Vibrio harveyi* BB120 by use of the composition of the invention was assessed. Axenically hatched *Artemia* were collected from the hatching bottle on a 100 μm sterile sieve and washed with FAASW. Artemia were transferred to sterile 50 mL test tubes containing 10 mL FAASW at a density of 2 Artemia/mL (=20 Artemia nauplii per tube). Autoclaved Aeromonas hydrophila LVS3 was added at 107 CFU/mL in each test tube as feed for the Artemia nauplii. The assay consisted of following treatments (n=5 per treatment):

neutral control (no addition of Archaea, nor Vibrio harveyi BB120)
positive control (only addition of Archaea)
negative control (only addition of Vibrio harveyi BB120)
test (addition of Archaea+addition of Vibrio harveyi BB120)

The Archaea and the pathogenic Vibrio harveyi BB120 were added at a density of 107 cells/mL (this equals 100 mg/L in case of the probiotic). The survival of the Artemia was determined after 48 h. After 48 h, the number of pathogenic Vibrios was determined in the test treatment (=addition of Archaea+addition of Vibrio harveyi BB120) by dilution plating on TCBS medium and incubating the plates at 28° C. for 48 hours.

Figure 6:
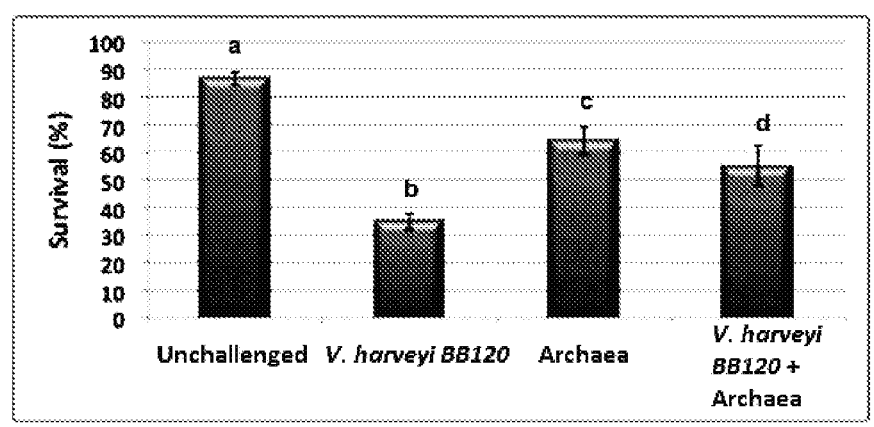
FIG. 6 shows results of the in vivo challenge test to assess the effect of Archaeabacteria on the survival (%) of *Artemia nauplii* exposed to pathogenic *Vibrio harveyi* BB120 for 48 h. Values represent means±standard error of the mean (n=5). Bars indicated with different letters are significantly different (One-Way Anova, $p \leq 0.05$)

The effect of the Archaeabacteria on the survival of the differentially treated Artemia nauplii is given in FIG. 6. The unchallenged Artemia nauplii showed an average survival of almost 90% and the Artemia nauplii challenged with V. harveyi BB120 showed a significantly lower survival of on average 35%. These are normal results for the gnotobiotic Artemia challenge system with V. harveyi challenge during 48 h. The application of Archaeabacteria alone resulted in a survival of on average 64% which was significantly lower than the unchallenged control. When Archaeabacteria was applied to Artemia nauplii that were challenged with the pathogenic V. harveyi BB120, the survival was significantly higher as compared to nauplii that were challenged with the pathogen but that were not treated with the product.

It was additionally observed that the Artemia nauplii in the treatment with Archaeabacteria seemed more active and larger than the Artemia nauplii in the unchallenged control treatment.

At the beginning of the trial the density of pathogens added as a challenge was on average $7.0 \times 10^6$ CFU mL$^{-1}$ (see Table 1). In the treatment with only Archaeabacteria no presence of vibrios could be detected, neither at the beginning nor at the end of the trial. At the end of the trial, the density of the pathogens when Archaeabacteria was added in combination with the challenge was on average $7.5 \times 10^6$ CFU mL$^{-1}$.

TABLE 1

Concentration of V. harveyi BB120 (as counted on TCBS agar) in the water at the beginning and end of the in vivo trial with Artemia nauplii to assess the effect of Archaeabacteria on the survival of Artemia nauplii exposed to pathogenic Vibrio harveyi BB120.

| Treatment | Initial concentration of V. harveyi BB120 (CPU mL$^{-1}$) | Final concentration of V. harveyi BB120 (CPU mL$^{-1}$) |
|---|---|---|
| Unchallenged control | ND | ND |
| V. harveyi BB120 | $7.0 \times 10^6 \pm 2.4 \times 10^5$ | / |
| Archaeabacteria | ND | ND |
| V. harveyi BB120 + Archaeabacteria | $7.0 \times 10^6 \pm 2.4 \times 10^5$ | $7.5 \times 10^6 \pm 1.2 \times 10^6$ |

From the results it can be concluded that Archaeabacteria provides a significant protection to Artemia nauplii challenged with the known aquaculture pathogen V. harveyi BB120. Due to absence of clearing zones in the in vitro plate trials and the fact that the number of V. harveyi BB120 did not decrease during the in vivo challenge trial, it cannot be concluded that this protection was due to a direct antimicrobial effect of the probiotic towards the pathogens. It was (qualitatively) observed, however, that the Artemia from the in vivo trial that were exposed to only Archaeabacteria seemed larger and more active than the Artemia nauplii from the control treatment (i.e. only fed with LVS3). This indicates that Archaeabacteria supported the development and growth, and as a consequence potentially also the disease resistance, of the Artemia nauplii during the trial.

Example 3

To demonstrate the effects of the bioactive supplement of the invention in the nutrition, growth, faecal pollutants and gut microbiome changes in fish, several experiments have been conducted on the herbivorous Ancistrus dolichopterus catfish.

Methods

Fish:

Young sibling Ancistrus dolichopterus catfish (1 month in age at the beginning of the experiment) were used. The gut of the juvenile fishes was initially inoculated with the faeces coming from their father to promote microbial colonization of the fish intestines in a homogenous manner. Fishes were maintained in 50 liters aquariums with an autonomous water filtration system. One quarter of the water was replaced every week. Fish wellbeing and normal behaviour was verified periodically.

Standard and Bioactive Feed Production:

Fishes were fed with a homemade feed composed of vegetables (spinach leaves, cucumber, zucchini, green peas and potatoes, representing 75% of total wet weight), white soybean paste (15% wet weight), and fish meat (10% wet weight). These ingredients were hashed and mixed to form a paste and pre-heated agar-agar was added and thoroughly mixed. The final paste was poured into plastic bags, flattened and frozen at −20° C. Small pieces were cut, defrosted and weighted to feed the fish.

To test the effects of the bioactive feed supplement, a batch of homemade feed including a low dose of bioactive feed supplement at a final concentration of $10^6$ Archaeabacteria cells per gram of feed was prepared (referred to as the Low dose supplemented feed). A batch of homemade feed including a high dose of bioactive feed supplement at a final concentration of $10^8$ Archaeabacteria cells per gram of feed (referred to as the High dose supplemented feed) was also prepared.

Juvenile Ancistrus catfish were divided into three experimental groups, with 20 specimens per group, and fed ad libitum 6 days per week as follows:

1. Control: standard homemade feed with no bioactive feed supplement
2. Low dose supplement: homemade feed with low dose of supplement
3. High dose supplement: homemade feed with high dose of supplement Fishes were kept under these feeding conditions for 4 months and three weeks.

Fish Weight Gain:

At day 1 of the feeding experiment, the 20 fishes per group were weighed to the nearest 5 mg. The fishes were subsequently weighed at six time points over a period of four months and two weeks.

Feed Conversion Ratio (FCR):

Four months after the start of the feeding experiment, 8 specimens of each of the 3 experimental groups were individually weighed and placed in individual 3-liters tanks with a reduced filtered water circulation (0.5 l/hour). Over a period of four days, each fish was given a precisely weighed amount of its respective feed, in the morning. The daily feed weight was about 100 mg. At day five in the morning, each fish was weighed, residual feed in the bottom of the tanks was weighed, and the faeces were collected and weighed. Total ingested feed during the 4-days period was calculated by summing up the daily feed weights and then subtracting the weight of residual feed. Fish weight gain during the 4-days period was calculated by subtracting the initial fish weight to the fish weight at day 5 in the morning. FCR is obtained by the weight of ingested feed during the 4-days period divide by the fish weight gain over the same period. FCR was calculated according to the rules presented in USAID Technical Bulletin #07.

Tank Water Quality Measurements:

Three months and three weeks after the start of the feeding experiment, and 6 hours after the feeding session of the day, 8 specimens of each of the 3 experimental groups were taken from their aquarium and placed in three small 3-liters tanks, one tank per group. These 3 tanks were previously filled with clean water coming from a same water reservoir to ensure homogenous initial water quality across the 3 groups. A sample of the initial water was kept for water quality subsequent analyses. The fishes received no feed for a period of 30 hours. After the 30 hours, 500 ml of tank water of each experimental group was collected to measure water quality parameters, while the fishes were replaced in their original respective aquariums. Using a photometer AL450 (Aqualytic) and the respective kits, the following water parameters were measured: phosphates, nitrites, pH, conductivity. Final phosphates and nitrites values were obtained after subtracting the values measured on the initial water. The 8 fishes per experimental group were weighed, and the final phosphates and nitrites values were given per gram of fish in the tank. This full procedure was replicated 3 times in total, with the same set of fishes, and at a 7 days interval.

Microbiome Metabarcoding:

Three months after the start of the feeding experiment, five specimens of the control group and five specimens of the High dose supplemented group were placed in individual 3-liters tanks filled with clean water, without water circulation. 2 hours later, faeces where collected for each specimen individually and placed directly into DNA extraction tubes of the PowerSoil DNA isolation kit (MoBio). After DNA extraction, the Prokaryotic (Bacteria and Archaea) 16S hypervariable regions V3-V4 was amplified by PCR using the primers Pro341F/Pro805R (excluding the illumina adapter sequences), published by Takahashi et al. (PLoS One, DOI: 10.1371/journal.pone.0105592, 2014). The 10 PCR products were purified using the High Pure PCR Product Purification Kit (Roche). A library was prepared for each of the 10 samples using the TruSeq Nano DNA Library Preparation Kit (illumina). The libraries were quantified by real-time quantitative PCR and pooled in equimolar amounts. The pool of libraries was sequenced using the MiSeq Reagent Nano Kit V2 (500 Cycle) on a paired-end, 2×250-bp cycle run on a MiSeq illumina instrument. Paired-end reads were controlled for quality using the illumina Real-Time Analysis software (v 1.17.28). Assembled reads were analyzed using the 16S Metagenomics analysis pipeline of illumina, as implemented in the BaseSpace illumina platform (version 1.0.1.0, 2016).

Results

The Bioactive Supplement Enhance *Ancistrus* Catfish Growth Rate:

The gut microbiome plays a central role in feed digestion and nutrient assimilation and a highly specialized microbial community has evolved in herbivorous animals to extract nutrients from their energy-poor plant diet. Supplementing the feed with beneficial microorganisms can improve nutrient assimilation and increase growth rate.

Figure 7:
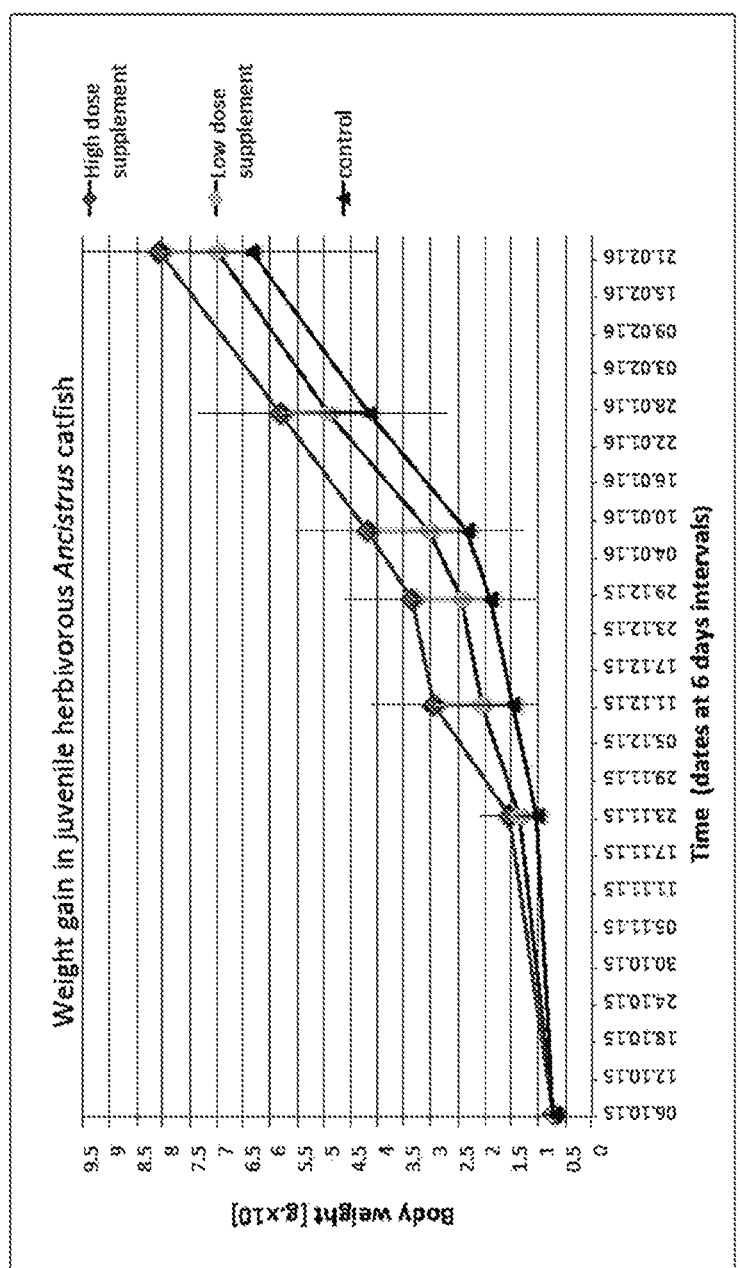
FIG. 7 shows the weight gain curve over a period of four months and two weeks for the three experimental groups: control, Low dose supplemented feed and High dose supplement feed. Data points correspond to the mean weight of the set of specimens of each group, with the standard deviation error bar.

*Ancistrus* catfishes fed with the bioactive supplement showed a higher growth rate, expressed as weight gain, as compared to the control group (FIG. 7). The difference in growth rate is, however, significant only between the control and the High dose supplemented feed. The nutritional and growth response is thus conditional to the dose of supplement in the feed.

The Bioactive Supplement Improves Feed Conversion Ratio in *Ancistrus* Catfish:

Improving the function of the gut microbiome by the adjunction of beneficial microorganisms can lead to an accelerated growth and weight gain during the period of growth. The feed conversion ratio (FCR), which measures the efficiency in converting feed mass into weight increase, was calculated for 8 specimens per experimental group over a period of 4 feeding days (Table 2). FCR values ranged from 24 to 207 for the control group, from 19.9 to 196.7 for the Low dose supplemented feed and from 6.5 to 139 for the High dose supplemented feed. These values are relatively elevated as compared to highly productive farmed fishes because *Ancistrus* catfishes have a slow growth due, in particular, to their highly developed and strong skeleton and their herbivorous diet. The FCR results indicate a significant increase in fishes fed with the High dose supplemented feed as compared to the control (t-Test, two tailed: t-stat=2.4178, df=9.69, P=0.0369). A slight FCR increase was also observed in fishes fed with the Low dose supplemented feed as compared to the control (t-Test, two tailed: t-stat=1.575, df=12, P=0.141). Thus, FCR improvement in *Ancistrus* catfishes depends on the dose of the bioactive supplement comprising Archaeabacteria and only the High dose supplemented feed showed a significant improvement as compared to the control.

TABLE 2

Data and results of the Feed Conversion Ratio (FCR) for the three experimental groups: control, Low dose supplement feed and the High dose supplemented feed.

| Specimen Number | fish initial weight (mg) | Feed weight (mg) | | | | residual feed | total ingested feed (food day 1 + 2 + 3 + 4) − residual food | fish final weight | fish weight gain (mg) | FCR total ingested feed/weight gain |
|---|---|---|---|---|---|---|---|---|---|---|
| | | day 1 | day 2 | day 3 | day 4 | | | | | |
| CONTROL: no bioactive supplement x | | | | | | | | | | |
| A1 | 831 | 100 | 103 | 118 | 123 | 56.1 | 387.9 | 833 | 2 | 193.95 |
| A2 | 943 | 104 | 106.6 | 105 | 115 | 71.2 | 358.9 | 945 | 2 | 179.45 |
| A3 | 1213 | 102 | 108.8 | 111 | 111 | 60.8 | 372.1 | 1216 | 3 | 124.0333333 |

TABLE 2-continued

Data and results of the Feed Conversion Ratio (FCR) for the three experimental groups: control, Low dose supplement feed and the High dose supplemented feed.

| Specimen Number | fish initial weight (mg) | Feed weight (mg) day 1 | day 2 | day 3 | day 4 | residual feed | total ingested feed (food day 1 + 2 + 3 + 4) − residual food | fish final weight | fish weight gain (mg) | FCR total ingested feed/weight gain |
|---|---|---|---|---|---|---|---|---|---|---|
| A4 | 633 | 110 | 104 | 102.5 | 128 | 39.1 | 405.6 | 647 | 14 | 28.97142857 |
| A5 | 605 | 109 | 100.5 | 109 | 115 | 32.5 | 401 | 608 | 3 | 133.6666667 |
| A6 | 497 | 101 | 100.4 | 132.5 | 84.7 | 9.9 | 408.7 | 514 | 17 | 24.04117647 |
| A7 | 527 | 103 | 104 | 125 | 94 | 11.1 | 414.9 | 529 | 2 | 207.45 |
| A8 | 532 | 104 | 103 | 126 | 93.5 | 11.3 | 415.2 | 535 | 3 | 138.4 |
| LOW DOSE bioactive supplement x | | | | | | | | | | |
| B1 | 1335 | 103.3 | 104.7 | 128 | 108 | 12.4 | 431.7 | 1339 | 4 | 107.925 |
| B2 | 748 | 105.3 | 108.5 | 122.3 | 125 | 10.1 | 450.8 | 785 | 37 | 12.18378378 |
| B3 | 996 | 102 | 103.3 | 124.1 | 117 | 16.1 | 430.3 | 1000 | 4 | 107.575 |
| B4 | 678 | 107 | 102 | 133 | 103 | 8.7 | 436.3 | 698 | 20 | 21.815 |
| B5 | 477 | 103.2 | 92.3 | 128 | 113 | 42.8 | 393.4 | 479 | 2 | 196.7 |
| B6 | 368 | 107.1 | 123.4 | 114 | 111 | 16.1 | 439.4 | 380 | 12 | 36.61666667 |
| B7 | 270 | 104.9 | 94.1 | 107.2 | 88.1 | 15.8 | 378.5 | 289 | 19 | 19.92105263 |
| B8 | 682 | 108 | 101 | 132 | 104 | 7.2 | 437.8 | 694 | 12 | 36.48333333 |
| HIGH DOSE bioactive supplement x | | | | | | | | | | |
| C1 | 638 | 108.6 | 109.6 | 100.5 | 127 | 28.2 | 417.5 | 641 | 3 | 139.1666667 |
| C2 | 926 | 100.5 | 101.4 | 103 | 112 | 6.3 | 411 | 978 | 52 | 7.903846154 |
| C3 | 847 | 104 | 102.6 | 103.1 | 112 | 18.1 | 403.2 | 852 | 5 | 80.64 |
| C4 | 1147 | 107.6 | 97 | 105.3 | 112 | 19.1 | 402.9 | 1151 | 4 | 100.725 |
| C5 | 988 | 101.7 | 100.4 | 103.2 | 115 | 14.2 | 406.3 | 993 | 5 | 81.26 |
| C6 | 728 | 109.4 | 100.4 | 121 | 109 | 14.1 | 425.6 | 782 | 54 | 7.881481481 |
| C7 | 570 | 108.1 | 101.3 | 119.8 | 97 | 12 | 414.2 | 634 | 64 | 6.471875 |
| C8 | 690 | 103.2 | 100.1 | 121 | 96.3 | 17.5 | 403.1 | 702 | 12 | 33.59166667 |

The Bioactive Supplement Reduces the Amount of Faeces in *Ancistrus* Catfish:

An improved digestion and nutrient assimilation triggered by the feed bioactive supplement is expected to reduce the weight of faeces produced per weight of ingested feed. Using the same data as for the calculation of the FCR, and by weighing the faeces produced at day five of the experiment, the ratio of faeces weight per weight of ingested feed was calculated (Table 3). The results show that the fishes fed with the bioactive supplement produce a lower amount of faeces than the control. T-tests of independent samples indicate that both the Low dose and the High dose supplemented feed resulted in a significant reduction of the weight of faeces per weight of ingested feed (Low dose: t-stat=2.227, df=12, P=0.023; High dose: t-stat=3.761, df=12, P=0.0014). This result suggest that the bioactive supplement will likely reduce the amount of faecal pollutants due to the simple reduction of faeces amount.

Figure 8:
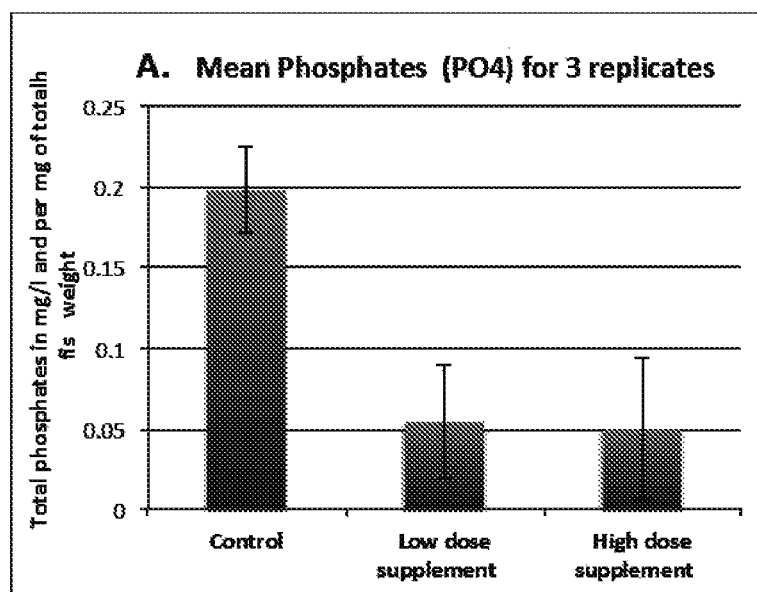
FIG. 8 shows the analysis of fish waste pollutants in water in the three experimental groups. A) Mean phosphate concentration for the 3 replicates. The presented phosphate values were obtained after subtracting the concentration measured in the water before the experiment, and are given as phosphates in mg/l and per mg. of total fish weight in the tank. B) Mean nitrites concentration for 3 replicates. The values presented are given as nitrites in mg/l. and per mg. of total fish weight in the tank.
Figure 8:
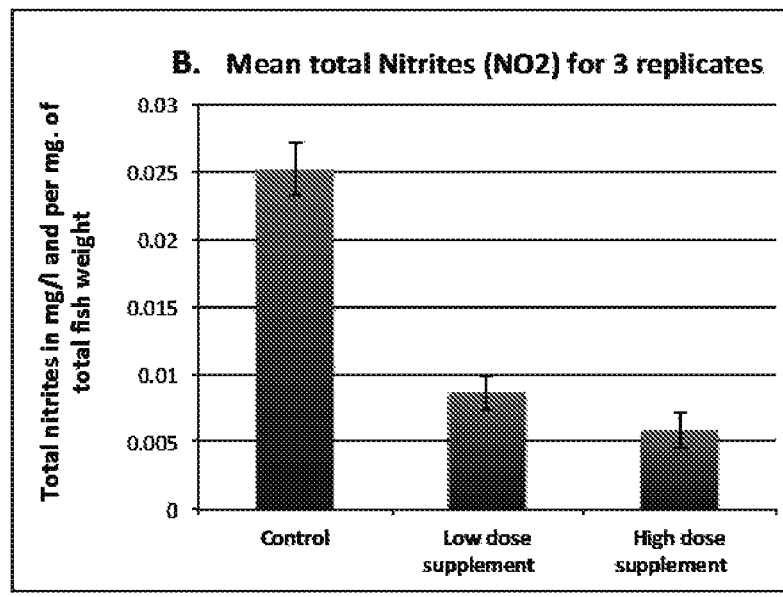

The Bioactive Supplement Reduces *Ancistrus* Catfish Waste Pollutants:

Animal faeces are a source of nitrites and phosphates pollutants. The presence of large quantities of nitrites and phosphates is indicative of wasted water pollution, with harmful effects on the environment. The effect of the bioactive supplement on the reduction of pollutants in faeces was tested on the herbivorous catfish *Ancistrus dolichopterus*. The results of the measurements of water quality parameters (FIG. 8) indicate that the concentration of phosphates and nitrites was significantly lower in the water of the tanks containing the fishes fed with the bioactive supplement (either the High dose supplemented feed or the Low dose supplemented feed) as compared to the water of the tank containing the control group of fishes (t-tests of two independent samples: phosphates in control versus Low dose supplemented feed, t-stat=6.478, df=2, P=0.0115;

TABLE 3

Faeces weight produced during the 4 feeding days of the FCR experiment, expressed as faeces weight per ingested feed weight × 100. The fish specimens and the total ingested feed weights are the same as in Table 1.

| CONTROL: no bioactive supplement x | | | LOW DOSE bioactive supplement x | | | HIGH DOSE bioactive supplement x | | |
|---|---|---|---|---|---|---|---|---|
| Specimen Number | total feces weight (mg) | feces weight// ingested feed weight*100 | Specimen Number | total feces weight (mg) | feces weight/ ingested feed weight*100 | Specimen Number | total feces weight (mg) | feces weight/ ingested feed weight*100 |
| A1 | 22.4 | 5.774684197 | B1 | 29.9 | 6.926106092 | C1 | 8.9 | 2.131736527 |
| A2 | 25.9 | 7.216494845 | B2 | 28.6 | 6.344276841 | C2 | 16.7 | 4.063260341 |
| A3 | 34.8 | 9.352324644 | B3 | 27.9 | 6.483848478 | C3 | 16.2 | 4.017857143 |
| A4 | 26.4 | 6.50887574 | B4 | 15.2 | 3.483841394 | C4 | 18.9 | 4.69099032 |
| A5 | 25.4 | 6.334164589 | B5 | 19.8 | 5.033045247 | C5 | 17.1 | 4.208712774 |
| A6 | 21.2 | 5.18717886 | B6 | 15.1 | 3.436504324 | C6 | 9 | 2.114661654 |
| A7 | 20.8 | 5.013256206 | B7 | 11.1 | 2.932628798 | C7 | 11 | 2.655721873 |
| A8 | 19.2 | 4.624277457 | B8 | 15.6 | 3.5632709 | C8 | 15.6 | 3.870007442 | phosphates in control versus High dose supplemented feed, t-stat=6.298, df=2, P=0.012; nitrites in control versus Low dose supplemented feed, t-stat=24.779, df=2, P=0.0008; nitrites in control versus High dose supplemented feed, t-stat=29.86, df=2, P=0.0006). No significant difference was observed between the two experimental doses of bioactive feed supplement (High dose or Low dose experimental feed).

Starting water pH was between 7.76 and 7.91. At the end of the experiment, water pH in the control group was in the range of 7.57 to 7.67, while in the Low and High dose supplemented feed, water pH was in the range of 7.59 to 7.85. At the end of the experiment, water conductivity (in µS/cm) was higher in the control group (280-283 µS/cm) as compared to the group with Low dose supplemented feed (275-277 µS/cm) or to the group with High dose suppletant difference is that the *Achaea* species composing the bioactive supplement is systematically present and in higher abundance (ranging from 0.005 to 0.225% of all assigned reads) in the microbiome of the fishes of the High dose supplemented feed group as compared to the microbiome of the fishes of the control group (ranging from 0 to 0.004% of all assigned reads). According to a t-test, this difference is significant (t-stat=2.532, df=7, P=0.019).

In view of the advantageous properties of the supplement shown in the examples it can be stated that the use of the bioactive food supplement can have an impact on farmed animals especially in terms of benefits on immune system as well as on digestive performances, but also on the amelioration of faecal waste quality, specifically with regards to nitrate content, an important pollutant that results from animal farming.

TABLE 4

Change in the frequency of the six most abundant classes of bacteria found in the control group, for five fishes of the control group and five fishes of the High dose supplemented feed group. The numbers represent the percentage of reads attributed to the given class of bacteria over the total number of reads.

| | Six most aboundant Classes in the control group (cummulative aboundance >93%) | | | | | | Cummulative |
|---|---|---|---|---|---|---|---|
| | Gammaproteobacteria | Flavobacteriia | Alphaproteobacteria | Betaproteobacteria | Sphingobacteriia | Actinobacteria | aboundance |
| control 1 | 46.18 | 16.57 | 13.86 | 8.97 | 6.57 | 1.04 | 93.19 |
| control 2 | 46.99 | 34.98 | 2.45 | 9.46 | 1.29 | 0.64 | 95.81 |
| control 3 | 38.87 | 28.71 | 9.53 | 10.42 | 5.53 | 0.878 | 93.938 |
| control 4 | 45.98 | 27.99 | 6.59 | 9.71 | 3.78 | 0.82 | 94.87 |
| control 5 | 47.35 | 28.78 | 5.75 | 9.34 | 2.84 | 0.387 | 94.447 |
| High dose 1 | 78.23 | 5.38 | 1.14 | 8.24 | 0.552 | 0.62 | 94.162 |
| High dose 2 | 80.51 | 6.18 | 0.76 | 5.25 | 0.239 | 0.94 | 93.889 |
| High dose 3 | 79.79 | 6.78 | 0.64 | 7.19 | 0.107 | 0.55 | 95.057 |
| High dose 4 | 78.58 | 8.55 | 0.82 | 6.49 | 0.29 | 0.86 | 95.59 |
| High dose 5 | 69.01 | 17.45 | 0.66 | 6.97 | 0.377 | 0.261 | 94.728 | mented feed (270-274 µS/cm). These results indicate a slight water acidification and an increased conductivity in the control as compared to the fishes fed with the bioactive supplement.

The Bioactive Supplement Changes the Microbiome of *Ancistrus* Catfish:

This experiment is aimed at characterizing the microbiota change induced by the bioactive probiotic x in *Ancistrus dolichopterus* catfish, as measured in fresh faeces. Fresh faeces of 5 specimens of the control group and five specimens of the High dose supplemented feed were collected and their microbiome was metabarcoded. The number of high quality paired-end reads ranged from 48'500 to 57'200 per specimen. The results of the metabarcode analysis indicate that the microbiome is markedly modified in the fishes fed with the bioactive supplement as compared to the control. This can be observed in the significant change in the frequency of the six more abundant classes of bacteria in the control group versus the High dose supplemented feed group, presented in Table 4 (Multivariate analysis of variance (MANOVA) test between the control group and the High dose group: Pillai Trace t-stat=0.984, F=29.98, df1=6, df2=3, P=0.009). The microbiome modification can also be appreciated by the diversity of bacterial and *Achaea* genera found in the samples, which is higher in the control group (range: 246 to 313 genera per sample) than in the High dose supplemented feed group (range: 179 to 267 genera per sample). A one-way (single factor) ANOVA analysis indicates that this difference is significant (within groups: SS=7272, df=8, MS=909; between groups SS=10112.4, df=1, MS=10112.4, F=11.125, P=0.0103). Another impor-

The invention claimed is:

1. An enriched animal feed composition comprising at least one population of at least one methanogenic Archaebacteria species, wherein the enriched animal feed composition comprises between $10^5$ and $10^8$ live Archaebacteria cells per gram, and
   the enriched animal feed composition at least one of increases animal growth rates and ameliorates the animal faecal waste impact on environment compared to standard non-enriched animal feeds.

2. The enriched animal feed composition according to claim 1, wherein the enriched animal feed composition is for animal farming.

3. The enriched animal feed composition according to claim 1, wherein the methanogenic Archaebacteria species is the *Methanosphaera stadtmanae* species or the *Methanobrevibacter smithii* species.

4. The enriched animal feed composition according to claim 1, wherein the enriched animal feed composition is in a solid form.

5. The enriched animal feed composition according to claim 1, wherein the at least one population of at least one Archaebacteria species is obtained by isolation from a rumen extract.

6. The enriched animal feed composition according to claim 2, wherein the animals are birds, mammals or aquatic animals.

7. A method of manufacturing an enriched animal feed composition according to claim 1, the method comprising the steps of:
   obtaining at least one population of at least one Archaebacteria species; and mixing the at least one population of at least one Archaebacteria species with a carrier.

8. The method according to claim 7, wherein the carrier comprises at least one selected from the group consisting of an aqueous solution, an oil, an Archaebacteria culture medium, and a rumen fluid.

9. The method according to claim 7, wherein the carrier is a liquid carrier, and further comprises the steps of:

adding between 1% to 10% w/v of a thickening agent to the liquid composition comprising the liquid carrier and the at least one population of at least one Archaebacteria species;

mixing the liquid composition to obtain a thickened solution; and drying the thickened solution to obtain a solid composition.

10. The method according to claim 9, wherein the thickening agent is at least one selected from the group consisting of sugar, starch, and gelatin.

11. A method of increasing animal growth rates comprising enriching animal feed with at least one population of at least one methanogenic Archae species, wherein the enriched animal feed comprises between $10^5$ and $10^8$ live Archaebacteria cells per gram of the animal feed.

12. A method of ameliorating faecal waste impact on environment comprising enriching animal feed with at least one population of at least one methanogenic Archae species, wherein the enriched animal feed comprises between $10^5$ and $10^8$ live Archaebacteria cells per gram of the animal feed.

13. The enriched animal feed composition according to claim 1, wherein microbial cells in the enriched animal feed composition are all Archaebacteria cells.

* * * * *